US005734013A

United States Patent [19]
Debernard et al.

[11] Patent Number: 5,734,013
[45] Date of Patent: Mar. 31, 1998

[54] PEPTIDES HAVING FARNESYL TRANSFERASE INHIBITING PROPERTIES AND STRAIN OF GENUS STREPTOMYCES FOR PRODUCING SAME

[75] Inventors: Jean-Jacques Debernard, Marolles En Brie; Thierry Flamant, Saint Maur; Didier Van Der Pyl, Saulx Les Chartreux, all of France

[73] Assignee: Rhone-Poulenc Rorer S.A., Antony Cedex, France

[21] Appl. No.: 716,193

[22] PCT Filed: Mar. 24, 1995

[86] PCT No.: PCT/FR95/00375

§ 371 Date: Sep. 27, 1996

§ 102(e) Date: Sep. 27, 1996

[87] PCT Pub. No.: WO95/26981

PCT Pub. Date: Oct. 12, 1995

[30] Foreign Application Priority Data

Mar. 30, 1994 [FR] France .................................. 94/03744

[51] Int. Cl.$^6$ .............................. C07K 7/06; C12P 21/02; C12R 1/465
[52] U.S. Cl. .................. 530/317; 435/71.1; 435/252.35; 514/9
[58] Field of Search .................... 530/317, 318; 435/71.1, 886; 514/9

[56] References Cited

FOREIGN PATENT DOCUMENTS

WO 96/09821  4/1996  WIPO .
WO 96/10035  4/1996  WIPO .
WO 96/10037  4/1996  WIPO .

OTHER PUBLICATIONS

Hancock, Anti–Ras drugs come of age. Current Biology, 3(11), 770–772 1993.

Hara et al. Identification of Ras farnesyltransferase inhibitors by microbal screening. Proc. Natl. Acad. Sci. USA, 90, 2281–2285 1993.

Internal Medicine, 4th Edition, Editor–In–Chief Jay Stein, Chapters 71–72, pp. 699–715 1992.

Journal of Antibiotics, vol. 46, No. 2, pp. 222–228, Feb., 1993 Omura Van Der Pyl Inokoshi Takahashi Takeshima Pepticinnamins, New Farnesyl–Protein Transferase Inhibitors Produced by an Actinomycete.

Journal of Antibiotics, vol. 46, No. 2, (pp. 229–234), Feb., 1993 Shiomi Yang Inokoshi Van Der Pyl Nakagawa Takeshima et al. Pepticinnamins, New Farnesly–Protein Transferase Inhibitors Produced by an Actinomycete.

*Primary Examiner*—Cecilia Tsang
*Assistant Examiner*—Michael Bozin
*Attorney, Agent, or Firm*—Michael B. Martin; Julie K. Smith; Raymond S. Parker, III

[57] ABSTRACT

A Steptomyces No. CBS 154.94 strain, mutants or derivatives thereof, and a method for preparing peptides using said strain, are disclosed. Novel peptides of general formula (1), pharmaceutical compositions containing same, and the use thereof in cancer therapy, are also disclosed.

12 Claims, No Drawings

PEPTIDES HAVING FARNESYL TRANSFERASE INHIBITING PROPERTIES AND STRAIN OF GENUS STREPTOMYCES FOR PRODUCING SAME

The present invention relates to a microorganism strain and to novel peptides which display farnesyl transferase inhibitory properties.

Activation of ras oncogenes is implicated in 10 to 30% of human cancers. The corresponding Ras protein is synthesized in vivo in the form of a cytosoluble precursor which is then modified post-translationally so as to confer on it its biological activity and to enable it to transform mammalian cells.

The first and obligatory step in these post-translational modifications consists of a farnesylation of the thiol group of a cysteine residue which is located in the carbonyl terminal group of Ras. This cysteine residue is part of the prenylation identification sequence CAAX, where C represents cysteine, A represents an aliphatic residue and X represents any amino acid.

The protein farnesyl transferase catalyses the transfer of a farnesyl group from farnesyl diphosphate to the Ras CAAX peptide. This farnesyl transferase protein recognizes tetrapeptides of the CAAX type which are located at the C-terminal end of the protein under the express stipulation that the fourth residue from the C-terminal end is a cysteine.

At the conclusion of this prenylation, the Ras protein possesses the biological activity which is required for transforming cells. The prenylation therefore appears to be necessary for regulating the biological activity of the Ras protein.

The discovery of compounds which inhibit its post-translational modification was rapidly seen to be a means for developing novel anti-cancer treatments.

Thus, genetic studies demonstrated that inhibition of the farnesylation of Ras prevented the Ras protein from locating in the membrane and consequently blocked its ability to transform normal cells into cancerous cells.

The principal object of the present invention is to propose novel inhibitors of farnesyl transferase.

More precisely, the present invention results from the isolation of a microorganism strain which belongs to the Streptomyces genus and which possesses properties which are particularly advantageous for producing peptides which display inhibitory properties with regard to the protein farnesyl transferase.

One aspect of the invention therefore relates to a Streptomyces strain which is characterized in that it is the microorganism Streptomyces CBS 154.94, one of its derivatives or one of its mutants.

Within the meaning of the present invention, derivative or mutant is understood to mean any strain which is obtained from the strain Streptomyces CBS 154.94 and which can be used for producing peptides which are in accordance with the invention and which, more particularly, display inhibitory properties with regard to the protein farnesyl transferase. In particular, such derivatives or mutants can be obtained by means of genetic (alteration of the DNA) or biochemical modifications. Different mutagenesis aids can be used for this purpose, such as, for example, non-specific aids:

physical agents (X-rays, ultraviolet rays, etc.), or
chemical agents (alkylating or bialkylating agents, intercalating agents, etc.),
or specific aids, such as the DNA-directed mutational insertion systems (transposons, retrotransposons, integrating plasmids, etc.).

Fermentation of this strain on a suitable culture medium and subsequent extraction of the corresponding fermentation broth enables peptides to be isolated which, although possessing a structure which is novel as compared with that of the conventional inhibitors of farnesyl transferase, are unexpectedly found to be of interest in this regard.

The present invention also relates to peptides which can be obtained by fermenting the Streptomyces CBS 154.94 strain, or one of its mutants, and extracting the corresponding fermentation broth.

The present invention also relates to a process for producing peptides according to which the strain Streptomyces CBS 154.94, or one of its derivatives or mutants, is cultured and at least one peptide is recovered.

The strain is fermented in a conventional manner, namely on a culture medium containing the substrates which are necessary for the development of the said microorganism and under appropriate temperature and aeration conditions. It is evident that determination of these conditions which are optimal for the development of the microorganism requires simple routine operations which are familiar to the skilled person.

For information only, the culture medium can consist of glucose, a yeast extract, a meat extract, NaCl, $CaCO_3$ and agar. The fermentation is preferably carried out at a temperature which is greater than the ambient temperature and, more particularly, between 25° C. and 30° C. The pH is of the order of 7 and the medium is aerated and shaken.

At the conclusion of the fermentation, the fermentation broth is recovered and centrifuged. The supernatant and the corresponding mycelial pellet are then extracted.

They are extracted using an appropriate organic solvent. This solvent is preferably ethyl acetate. The respective organic phases are pooled, concentrated and then chromatographed so as to isolate the active peptides. Example 1, which is presented below, gives a detailed account of this process for isolating the peptides from the fermentation broth.

More specifically, the present invention relates to peptides of the general formula I

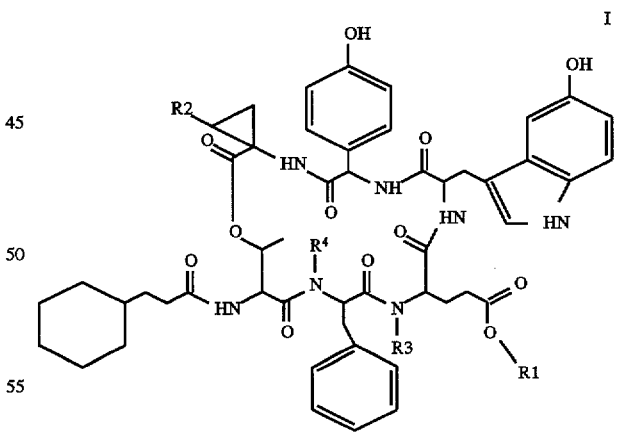

in which:
R1, R2, R3 and R4 represent, independently of each other, a hydrogen atom or a straight-chain or branched $C_1$ to $C_4$ lower alkyl group.

More specifically, the peptides are compounds of the general formula I in which R4 represents a methyl group and R3 represents a hydrogen atom.

As peptides which are preferred in accordance with the invention, mention may be made, more specifically, of the following peptides 1, 2 and 3:

In the case of peptide No. 1, R1, R2 and R3 represent a hydrogen atom and R4 represents a methyl group.

In the case of peptide No. 2, R2 and R4 represent a methyl group and R1 and R3 represent a hydrogen atom.

In the case of peptide No. 3, R1, R2 and R4 represent a methyl group and R3 represents a hydrogen atom.

Unexpectedly, these peptides exhibit significant in-vitro activity in the farnesyl transferase inhibition test.

The principle of SPA (scintillation proximity assay) technology is applied to assaying the enzymic activity of farnesyl transferase. According to this method, farnesyl transferase inhibitory activity is determined by the quantity of ($^3$H)-farnesyl which is transferred from ($^3$H)-farnesyl pyrophosphate (($^3$H) FPP) to a biotinylated acceptor substrate.

The present invention also relates to the use of the peptides according to the invention in anti-cancer treatments.

It furthermore relates to pharmaceutical compositions which contain an adequate quantity of at least one peptide according to the invention, mixed together with one or more inert or physiologically active, pharmaceutically acceptable adjuvants.

1 Materials and Methods

A sample of the Streptomyces strain which was in accordance with the invention and which was employed in the example presented below was deposited and registered in the Centraalbureau voor Schimmel culturen (Central bureau for mould cultures) (CBS) at Baarn, Netherlands, under number CBS 154.94, under the conditions of the Budapest Treaty.

Method Employed for Detecting Active Metabolites: Scintillation Proximity Assay (SPA) Test for Farnesyl Transferase Inhibition The principle of SPA technology (H. E. Bart and E. B. Greenwald, J. Nucl. Med., 20, 1062–1065, 1979 and Nelson N., Analytical Biochemistry, 165, 287–293, 1987) is applied to assaying the enzymic activity of farnesyl transferase (Ftase). This enzyme was partially purified from human THP1 cells (Fromage N., Guitton J. D., Joyeux C., Desanlis F., Boniface O., Soria H. M., Boucher F., Cleft F. F., Crespo A., Duchesne M., Lavayre J., Tocque B, Van Der Pyl D., Mayaux J. F., Becquart J., 5th European Meeting of GFBC on bio-chromatography and molecular biology, May 12–14, 1992, France). The acceptor substrate, which is biotinylated, is a peptide of 11 amino acids corresponding to the terminal sequence of B lamin (BLB). The donor substrate, farnesyl pyrophosphate, is labelled with tritium ($^3$HFPP). The enzyme transfers the $^3$HFPP to the biotinylated acceptor substrate and, once the reaction has been stopped, the farnesylated peptide is captured by beads which encapsulate a fluorescent scintillant and which are coupled to streptavidin (Amersham kit TRKQ7010®). The radio-labelled peptide excites the beads, which then emit light which is quantified in a solid-liquid scintillation counter (Topcount®, Packard).

The SPA reaction is started by adding 40 µl of Ftase (2 µg) to a microtitre plate which contains 20 µl of BLB (0.1 µM), 20 µl of $^3$HFPP (0.12 µM) and 20 µl of assay buffer 50 mM Hepes, pH 7.5, 5 mM MgCl$_2$, 5 mM DTT, 20 mM KCl, 0.01% triton X100 (control) or 20 µl of sample diluted in assay buffer (screening). The plate is incubated at 37° C. for 60 minutes and the reaction is stopped by adding 150 µl of stopping reagent containing the SPA beads. The plate is sealed with an adhesive film, left at ambient temperature for 30 minutes in order to reach equilibrium, and then counted in the Topcount counter. The results are counted in disintegrations per minute, dpm, and expressed as % inhibition in comparison with the control enzyme (after substracting the blank). The IC$_{50}$ values of the compounds are calculated by non-linear regression.

EXAMPLE 1

Preparation of active Metabolites According to the Invention from the Streptomyces CBS 154.94 Strain A 2000 ml Erleumeyer flask, which contains 250 ml of medium (5 g/l peptones, 5 g/l yeast extract, 5 g/l meat extract, 15 g/l glucose, 5 g/l NaCl, 3 g/l CaCO$_3$, 1 g/l agar, pH 7.0) is seeded with a culture of Streptomyces CBS 154.94 which is in the form of a frozen liquid culture. The flask is shaken at 150 rev/min in a shaker which is thermostated at 28° C.

After 72 hours, 64% of this culture is transferred to a 6000 ml round-bottomed flask which contains 2000 ml of the same medium. This round-bottomed flask, which is provided with 2 side necks (one for seeding, the other for inoculating the fermenter) is stirred at 28° C. on a magnetic stirrer at approximately 1000 revolutions per minute. After 72 hours of incubation, the whole of this culture is transferred in a sterile manner into a 100 liter production fermenter containing 60 liters of previously sterilized medium (120° C. for 20 minutes) (20 g/l Alburex® N, 15 g/l glycerol, 2 g/l CaCO$_3$). The culture is maintained for 91 hours at a temperature of 28° C. and a pressure of 0.4 bar, while being stirred at 400 rev/min and aerated at the rate of 2 m$^3$/hr. 56.2 kg of broth are centrifuged using a Sharples AS16® centrifuge. This results in an aqueous supernatant and a mycelial pellet. The supernatant is extracted twice with 1 volume of ethyl acetate. Following separation of the phases, the organic phase is concentrated down to 2 liters under reduced pressure.

The mycelial pellet is taken up in 40 liters of an 80:20 mixture of acetone and water for the purpose of disintegrating it over a period of 2 hours. The cellular debris are removed by filtration through a sintered glass funnel and the filtrate is concentrated in vacuo down to a volume of 6 liters in order to remove the acetone. The 6 liters of aqueous phase (the measured pH is 5.8) are extracted twice with 15 liters of ethyl acetate. Following separation of the phases, the organic phase is concentrated down to 2 liters under reduced pressure.

The ethyl acetate extracts which are derived from treating the filtrate and the mycelium are pooled and evaporated, leading to an oily extract of 57 g. This extract is dissolved in 150 ml of butanol and then precipitated by adding 1350 ml of n-heptane while stirring vigorously. Following separation of the phases, the supernatant is removed and the precipitate which has been formed is separated by filtration through a sintered glass funnel. An extract of 21.7 g, which has an IC$_{50}$ of less than 3 µg/ml, is obtained after drying overnight in a vacuum oven.

EXAMPLE 2

Isolation and Characterization of Active Metabolites

The extract which is obtained in accordance with the previous example is dissolved in 150 ml of a 95:5 mixture of CH$_2$Cl$_2$ and MeOH and chromatographed on silica gel (180×200 mm column which is provided with a frit and which contains 650 g of Amicon® 40–60 µm silica gel which has been packed in vacuo).

The elution is carried out stepwise using the following ratios and quantities of CH$_2$Cl$_2$/MeOH:

90:05 v/v 1000 ml for fraction 1
90:10 v/v 1000 ml for fraction 2
80:20 v/v 1000 ml for fraction 3

70:30 v/v 1000 ml for fraction 4
60:40 v/v 1000 ml for fraction 5
50:50 v/v 1000 ml for fraction 6

After evaporating fractions 4 and 5 under reduced pressure, 4.82 g of active extract are obtained having an $IC_{50}$ in the vicinity of 1 μg/ml.

The following purification step consists of liquid chromatography on a column of $C_{18}$-grafted silica gel: the previous active extract, which has been redissolved in a 10:90 mixture of MeOH and $H_2O$ is trickled, at a rate of 10 ml/min, into a 300 ml Analytichem International vessel containing 160 ml of 40–63 μm Econosil prep $C_{18}$ HL Alltech® support. Elution is carried out using a 10 to 100% mixture of methanol in water. The gradient is produced using 500 ml steps which are in each case increased by a factor of 10. At this stage, the 10 fractions which are obtained can be analysed by thin layer chromatography on a Merck 60 F 254® silica gel plate using AcOEt/EtOH/$H_2O$ 50:15:10 (v:v:v) as the eluent. In this system, the sought-after metabolites migrate at a frontal ratio ($R_f$) of between 0.6 and 0.70, are visible under UV at 254 nm, and appear mauve when sprayed with sulphuric vanillin.

The fractions obtained after eluting with the 70:30 and 80:20 (v:v) MeOH/$H_2O$ mixtures mainly contain the active metabolites; the first fraction, of 1948 mg. and the second fraction, of 704 mg, have an $IC_{50}$ of about 0.7 μg/ml.

The purification continues with high pressure liquid chromatography: the 2 previous fractions are concentrated under reduced pressure and the residues are taken up in the minimum quantity of methanol so as to obtain a final concentration of about 50 mg/ml. For each chromatography, 2 ml of this solution is injected into an HPLC apparatus with the following specification:

column 250×25 mm, 5 μm Nucleosil SFCC $C_{18}$®
flow rate of 10 ml/min
A/B, 50:50, v:v, isocratic elution
 A: $H_2O$ containing 0.05% TFA
 B: $CH_3CN/H_2O$, 95:5 (v:v), containing 0.05% TFA
UV detection at 230 nm.

The cyclic peptides 1, 2 and 3 are eluted and collected separately, with respective retention times of 24 min, 30 min and 45 min.

At the conclusion of numerous HPLC injections and separations under the above-described conditions, we isolate 3 active fractions which respectively contain metabolites 1, 2 and 3 according to the invention. After evaporating off the acetonitrile under reduced pressure, the 3 fractions are trickled separately through a Mega Bond Elut $C_{18}$ Varian column, which is then rinsed with distilled water until the pH of the effluent is neutral; elution is then carried out using approximately 10 ml of methanol.

After evaporating the methanolic eluates under reduced pressure, we respectively obtain:

TABLE I

|    | 1    | 2      | 3      |
|----|------|--------|--------|
| R1 | H    | H      | $CH_3$ |
| R2 | H    | $CH_3$ | $CH_3$ |
| R3 | H    | H      | H      |
| R4 | $CH_3$ | $CH_3$ | $CH_3$ |
| QUANTITY | 5 mg | 214 mg | 243 mg |

The structures of each of the peptides were determined by mass spectrometry, infra-red spectroscopy and nuclear magnetic resonance ($^1H$ and $^{13}C$).

EXAMPLE 3
Determination of the Inhibitory Activity on the Farnesyl Transferase Protein For each metabolite, this activity is assessed using the method described in the previous section entitled materials and methods. The results are presented in Table II below.

TABLE II

| IDENTIFICATION OF THE ACTIVE METABOLITES | | | | |
|---|---|---|---|---|
|  | CVFM* | 1 | 2 | 3 |
| $IC_{50}$ | 0.052 μM | 626 nM | 538 nM | 1.3 μM |

*Peptide (cysteine-valine-phenylalanine-methionine) which is used as a control in the measurements of farnesyl transferase activity.

We claim:
1. Streptomyces strain No. CBS 154.94 and its mutants or derivatives.
2. A peptide, characterized in that it conforms to formula I

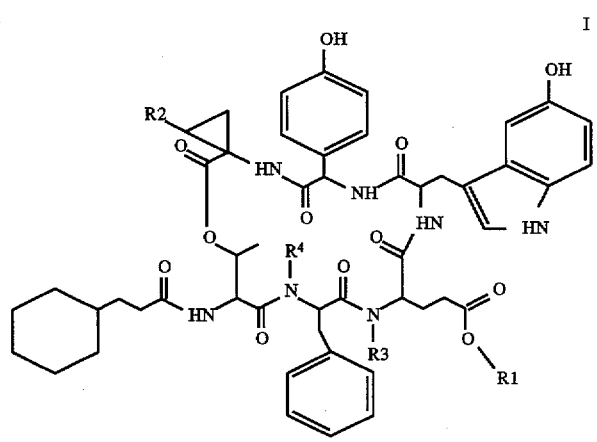

in which:
R1, R2, R3 and R4 represent, independently of each other, a hydrogen atom or a straight-chain or branched $C_1$ to $C_4$ lower alkyl group.
3. A peptide according to claim 2, wherein R4 is a methyl group and R3 is a hydrogen atom.
4. A peptide according to claim 2 wherein R1, R2 and R3 are hydrogen atoms and R4 is a methyl group.
5. A peptide according to claim 2 wherein R2 and R4 are methyl groups and R1 and R3 are hydrogen atoms.
6. A peptide according to claim 2 wherein R1, R2 and R4 are methyl groups and R3 is a hydrogen atom.
7. A peptide according to claim 2, which exhibits farnesyl transferase inhibiting activity.
8. A peptide which is obtained by fermenting a Streptemyces strain according to claim 1, and extracting the corresponding fermentation broth.
9. A process for producing peptides wherein a streptomyces strain according to claim 1 is cultured, the fermentation broth is extracted, and at least one peptide having farnesyl transferase inhibiting activity is recovered.
10. A composition comprising at least one peptide according to claim 2 admixed with one or more pharmaceutically acceptable adjuvants.
11. A method of treating cancer comprising the administration of a peptide according to claim 2.
12. A method of inhibiting farnesyl transferase comprising the administration of a peptide according to claim 2.

* * * * *

UNITED STATES PATENT AND TRADEMARK OFFICE
CERTIFICATE OF CORRECTION

PATENT NO.    : 5,734,013
DATED         : March 31, 1998
INVENTOR(S)   : Jean-Jacques Debernard et. al.

It is certified that error appears in the above-identified patent and that said Letters Patent is hereby corrected as shown below:

In column 6, line 19, replace "characterized in that it conforms to" with --of--.

In column 6, line 59, replace "at least one peptide according to" with --a peptide of--.

In column 6, line 62, insert --ras-dependent-- in front of "cancer".

Signed and Sealed this

Twenty-third Day of June, 1998

Attest:

BRUCE LEHMAN

*Attesting Officer*     *Commissioner of Patents and Trademarks*